US009232976B2

(12) United States Patent
Fortier et al.

(10) Patent No.: US 9,232,976 B2
(45) Date of Patent: Jan. 12, 2016

(54) MAGNETIC INTERFERENCE REDUCING SURGICAL DRAPE

(75) Inventors: Louis-Philippe Fortier, Anjou (CA); Valérie Zaphiratos, Montréal (CA); Howard Burman, Montréal (CA); Daniel Spooner, Lachine (CA); René Gosselin, Longueuil (CA); Richard Côté, Longueuil (CA)

(73) Assignee: RSEM LIMITED PARTNERSHIP, Montreal (CA)

( * ) Notice: Subject to any disclaimer, the term of this patent is extended or adjusted under 35 U.S.C. 154(b) by 357 days.

(21) Appl. No.: 13/805,448

(22) PCT Filed: Jun. 23, 2011

(86) PCT No.: PCT/CA2011/050387
§ 371 (c)(1),
(2), (4) Date: Mar. 1, 2013

(87) PCT Pub. No.: WO2011/160236
PCT Pub. Date: Dec. 29, 2011

(65) Prior Publication Data
US 2013/0199544 A1    Aug. 8, 2013

Related U.S. Application Data

(60) Provisional application No. 61/357,722, filed on Jun. 23, 2010, provisional application No. 61/434,986, filed on Jan. 21, 2011.

(51) Int. Cl.
*A61B 19/08* (2006.01)
*A61B 19/10* (2006.01)
(Continued)

(52) U.S. Cl.
CPC ............... *A61B 19/10* (2013.01); *A61C 19/00* (2013.01); *A61D 1/00* (2013.01); *H01F 7/0252* (2013.01);
(Continued)

(58) Field of Classification Search
USPC ........................................... 128/852
See application file for complete search history.

(56) References Cited

U.S. PATENT DOCUMENTS 3,483,494 A    12/1969 Cromie
3,727,658 A    4/1973 Eldridge, Jr.
(Continued)

FOREIGN PATENT DOCUMENTS

EP    0 081 225 A1    6/1983
WO    00/48526 A1    8/2000
(Continued)

*Primary Examiner* — Ophelia A Hawthorne
(74) *Attorney, Agent, or Firm* — Norton Rose Fulbright Canada LLP

(57) ABSTRACT

A magnetic drape comprises a drape body made of a flexible material. The drape body has a panel portion having an undersurface adapted to be laid on an uneven body and a top surface, and a given thickness between the undersurface and the top surface. A plurality of magnet units are within the flexible material of the drape body, with each said magnet unit comprising a shielding material in the shape of a cup oriented to have a bottom wall facing toward the undersurface of the drape body, and a magnet received at least partially in the cup. The magnet comprises two or more sections arranged to expose opposite polarity on a top surface of the magnetic drape, with each said section having opposite polarities oriented vertically.

19 Claims, 11 Drawing Sheets

(51) Int. Cl.
  *A61C 19/00* (2006.01)
  *A61D 1/00* (2006.01)
  *H01F 7/02* (2006.01)
  *A61B 17/00* (2006.01)
  *A61B 19/00* (2006.01)

(52) U.S. Cl.
  CPC ...... *A61B 19/088* (2013.01); *A61B 2017/00876* (2013.01); *A61B 2019/4036* (2013.01); *A61B 2019/5441* (2013.01)

(56) References Cited

U.S. PATENT DOCUMENTS

| | | | |
|---|---|---|---|
| 4,185,262 A | | 1/1980 | Watanabe |
| 4,373,629 A | | 2/1983 | Ulin et al. |
| 4,524,767 A | | 6/1985 | Glassman |
| 4,944,311 A | * | 7/1990 | Eldridge et al. ............ 128/849 |
| 5,195,538 A | | 3/1993 | Eldridge |
| 5,538,495 A | | 7/1996 | Ardizzone |
| 5,578,359 A | * | 11/1996 | Forbes et al. ............ 428/131 |
| 6,522,145 B1 | * | 2/2003 | Damadian et al. ........... 324/318 |
| 2002/0050311 A1 | | 5/2002 | Palumbo |
| 2002/0084008 A1 | | 7/2002 | Limoges et al. |
| 2002/0088515 A1 | | 7/2002 | Aust et al. |
| 2003/0234181 A1 | | 12/2003 | Palumbo |
| 2004/0112486 A1 | | 6/2004 | Aust et al. |
| 2005/0205425 A1 | | 9/2005 | Palumbo |
| 2006/0135281 A1 | | 6/2006 | Palumbo |
| 2006/0135282 A1 | | 6/2006 | Palumbo |
| 2006/0160636 A1 | | 7/2006 | Palumbo |
| 2006/0292388 A1 | | 12/2006 | Palumbo |
| 2007/0281176 A1 | | 12/2007 | Palumbo |
| 2008/0090066 A1 | | 4/2008 | Palumbo |
| 2008/0107805 A1 | | 5/2008 | Palumbo |
| 2008/0119307 A1 | | 5/2008 | Palumbo |
| 2008/0254310 A1 | | 10/2008 | Palumbo |
| 2009/0027149 A1 | | 1/2009 | Kocijan |
| 2009/0159451 A1 | | 6/2009 | Tomantschger et al. |
| 2009/0267717 A1 | * | 10/2009 | Baskett ..................... 335/285 |
| 2009/0298624 A1 | | 12/2009 | Palumbo |
| 2010/0007449 A1 | | 1/2010 | Tait et al. |
| 2010/0028714 A1 | | 2/2010 | Palumbo |
| 2010/0076556 A1 | | 3/2010 | Tomantschger et al. |
| 2010/0239801 A1 | | 9/2010 | Elia et al. |
| 2010/0291381 A1 | | 11/2010 | Elia et al. |
| 2010/0304063 A1 | | 12/2010 | McCrea et al. |
| 2010/0304065 A1 | | 12/2010 | Tomantschger et al. |
| 2010/0304171 A1 | | 12/2010 | Tomantschger et al. |
| 2010/0304172 A1 | | 12/2010 | Facchini et al. |
| 2010/0304179 A1 | | 12/2010 | Facchini et al. |
| 2010/0304182 A1 | | 12/2010 | Facchini et al. |
| 2010/0307642 A1 | | 12/2010 | Palumbo |
| 2011/0003171 A1 | | 1/2011 | Palumbo |

FOREIGN PATENT DOCUMENTS

| | | |
|---|---|---|
| WO | 20040105528 A2 | 9/2004 |
| WO | 20080141137 A2 | 11/2008 |

* cited by examiner

MAGNETIC INTERFERENCE REDUCING SURGICAL DRAPE

CROSS-REFERENCE TO RELATED APPLICATIONS

The present application claims priority on U.S. Provisional Application No. 61/357,722, filed on Jun. 23, 2011, and No. 61/434,986, filed on Jan. 21, 2011, both incorporated herein by reference.

FIELD OF THE APPLICATION

The present application relates to the field of medical devices used during surgical procedures, interventions and treatments, and more particularly to a magnetic drape used in the surgical room, intervention room or treatment room for holding instruments in close vicinity to the treatment site on a patient.

BACKGROUND OF THE ART

Surgeons and medical professionals and personnel (e.g., doctors, veterinarians, dentist, nurses) use a plurality of instruments in performing surgery/treatment such as scalpels, forceps, sharps, scissors, clamps, needles, etc. The various instruments each have a specific function during surgery/treatment. Rigid trays are commonly used in order to support the plurality of instruments during surgery/treatment. The trays are typically kept horizontal by a stand or other structure so as to be relatively close to the surgical/treatment site. Medical personnel is often required to select and hand the instruments to the surgeon from the tray. Oftentimes, a nurse or the like is dedicated to selecting and handing instruments as requested by the surgeon.

It also has been common for medical personnel to place instruments directly on the patient surface for easy access to the instruments, and to create a transfer zone close to the treatment site. Such hands-free practice reduces the risk of percutaneous injury to medical personnel as well as the possibility of dropping the instruments as a result of being passed back and forth. However, as the patient usually represents an uneven surface, instruments may not be retained properly on the patient due to the effect of gravity and may roll or slide off the patient onto the floor.

A magnetic mat, magnetic drape or surgical drape (reusable in that it can be sterilized or single use) has been used into surgical rooms for a number of years as an alternative, in supplement or in combination to rigid trays for holding instruments or placing the instruments on the patient surface. One example thereof is the MagnaDrape™. The MagnaDrape™ consists of a flexible instrument-holding drape made of silicone, typically 12 inches by 16 inches, within which a plurality of permanent magnet units are positioned. The magnet units of the MagnaDrape™ are embedded or sandwiched in the drape. The flexible nature of the drape allows it to be laid onto uneven surfaces such as the body of the patient, in close proximity to the surgical or treatment site. The permanent magnet units of the MagnaDrape™ produce a magnetic field that will attract the surgical instruments and retain them on the drape even if the drape is not horizontal. As the permanent magnets are raised, there is defined free space between the permanent magnet units to facilitate the grasping of instruments. As they are typically made of ferromagnetic material, the surgical instruments do not have to be treated prior to being used with the MagnaDrape™ other than to be sterilized. Accordingly, with the MagnaDrape™, the surgical instruments may be retained in close proximity to or on a patient without the need for a support structure such as a stand.

However, the presence of permanent magnet units produces magnetic fields. The magnetic fields may have an effect on nearby electronic devices, implanted devices, or on the patient. For instance, a magnetic field of a given magnitude may alter the operation of implanted electronic devices used for stabilizing and/or controlling physiological parameters such as pacemakers, defibrillators, insulin pumps or regulators, pain control devices, any programmable medical devices or electronic devices, etc. Such magnetic fields can also affect the blood flow of the patient. In some instances, it is desired to reduce or avoid such side effect.

SUMMARY OF THE APPLICATION

It is an aim of the present disclosure to provide a magnetic drape that addresses issues associated with the prior art.

It is an aim of the present disclosure to provide a novel magnetic drape.

It is a further aim of the present disclosure to provide a magnetic drape producing a magnetic flux density of substantially lower magnitude on its support side than that on its exposed side so as to reduce magnetic interferences with implanted electronic devices.

It is a still further aim of the present disclosure to provide a magnetic drape producing a magnetic flux density of less than 10 Gauss on its support side.

Therefore, in accordance with the present application, there is provided a magnetic drape comprising a drape body made of a flexible material, the drape body having a panel portion having an undersurface adapted to be laid on an uneven body and a top surface, and a given thickness between the undersurface and the top surface; and a plurality of magnet units within the flexible material of the drape body, with each said magnet unit comprising a shielding material in the shape of a cup oriented to have a bottom wall facing toward the undersurface of the drape body, and at least one magnet received at least partially in the cup, the at least one magnet comprising at least two sections arranged to expose opposite polarity on a top surface of the magnetic drape, with each said section having opposite polarities oriented vertically.

Further in accordance with the present disclosure, the magnet units each have any one of a circular shape and a rectangular shape.

Still further in accordance with the present disclosure, the cups each have a circular shape, and further comprising two sections of magnets in each said cup, each said section having a semi-circular shape.

Still further in accordance with the present disclosure, the cups each have a circular shape, and further comprising four sections of magnets in each said cup, each said section having a quarter shape, with the sections exposing a N-S-N-S sequence of opposite poles in the top surface of the magnet unit.

Still further in accordance with the present disclosure, the cups each have a circular shape, and further comprising six sections of magnets in each said cup, each said section having a sixth shape, with the sections exposing a N-S-N-S-N-S sequence of opposite poles in the top surface of the magnet unit.

Still further in accordance with the present disclosure, the cups each have a circular shape, and further comprising eight said sections in each said cup, with the sections exposing a N-S-N-S-N-S-N-S sequence of opposite poles in the top surface of the magnet unit.

Still further in accordance with the present disclosure, the cups each have a circular shape, and further wherein the at least one magnet comprises three sections in each said cup, each said section having an elongated shape with the sections arranged side by side to define a circular shape, with the magnets exposing a sequence of opposite poles in the top surface of the magnet unit.

Still further in accordance with the present disclosure, the cups each have a circular shape, and further wherein the at least one magnet comprises three sections in each said cup, each said section having an elongated shape with the sections arranged side by side to define a circular shape, with lateral sections exposing opposite poles in the top surface of the magnet unit, and a central section being oriented relative to the lateral sections to create a Halbach effect.

Still further in accordance with the present disclosure, the cups each have a rectangular shape, and wherein the at least one magnet comprises two sections in each said cup, each said section having an elongated shape with the sections arranged side by side to define a rectangular shape.

Still further in accordance with the present disclosure, the cups each have a rectangular shape, and wherein the at least one magnet comprises two sections in each said cup, each said section having a square shape with the sections arranged side by side to define a rectangular shape.

Still further in accordance with the present disclosure, the cups each have a rectangular shape, and wherein the at least one magnet comprises four sections in each said cup, each said section having a square or rectangular shape with the sections arranged side by side to define a rectangular shape.

Still further in accordance with the present disclosure, the cups each have a circular shape with at least two cavities, and further comprising one of said sections of magnet in each said cavity of the cups.

Still further in accordance with the present disclosure, the cavities have one of a circular shape and a triangular shape.

Still further in accordance with the present disclosure, shielding means are connected to or incorporated in the drape body below the plurality of magnet units.

Still further in accordance with the present disclosure, the shielding means is at least one of a shielding sheet, a shielding mesh, a shielding material, and shielding particles.

Still further in accordance with the present disclosure, at least one of a fluorescent and phosphorescent coating or additive is on the top surface of the drape body.

Still further in accordance with the present disclosure, the magnet units project upwardly from the top surface of the panel portion of the drape body.

Still further in accordance with the present disclosure, the given thickness of the panel portion is at least ⅛ in such that a magnetic flux density at the undersurface of the drape body is less than 10 Gauss.

Still further in accordance with the present disclosure, the given thickness of the panel portion is sized to keep the magnet units at a distance of at least ⅛ in from an electronic device in a patient when the magnetic drape is laid on the patient, such that a magnetic flux density is less than 10 Gauss at the electronic device.

DESCRIPTION OF PREFERRED EMBODIMENTS

Figure 1:
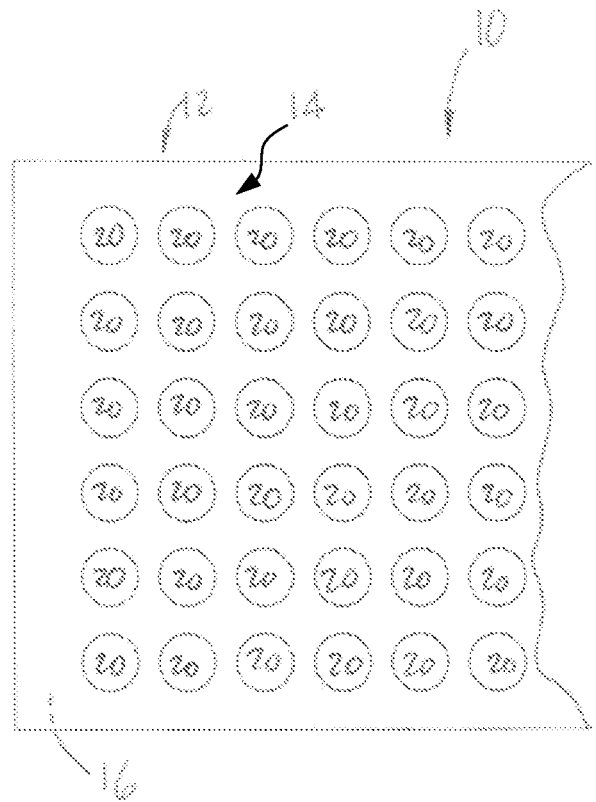
FIG. 1 is a top plan view, segmented, of a magnetic drape in accordance with an embodiment of the present disclosure.
Figure 2:
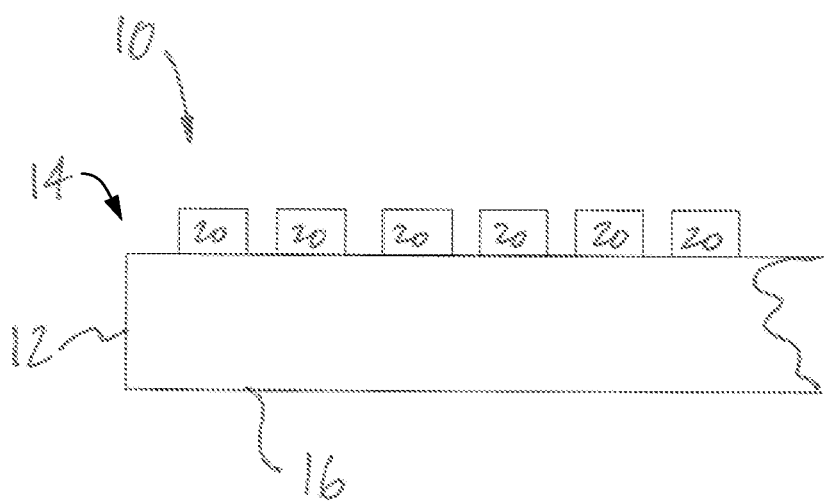
FIG. 2 is a schematic side elevation view of the magnetic drape of FIG. 1.

Referring concurrently to FIGS. 1 and 2, a magnetic drape in accordance with an embodiment of the present disclosure is generally shown at 10. The magnetic drape 10 may be used to support instruments in surgery, treatment, dentistry, veterinary medicine, or in any other applications. For simplicity purposes, the description below will generally refer to the use of the magnetic drape 10 to support instruments in surgery, but it will be understood that the magnetic drape 10 may be used in other applications. Moreover, the term "drape" is used, but is not meant to be limitative. The drape is also know as a support mat, panel, etc.

The magnetic drape 10 has a drape body 12 with a top surface 14 and an undersurface 16. The drape body 12 is made of a semirigid or flexible material and may also be known as a pad, a drape, a carpet or the like. Materials that may be used include nonrestrictively various medical-grade polymers and elastomers such as silicone, rubbers, etc., depending on the specifications of use of the magnetic drape 10 (e.g., reusable and sterilizable, single-use drape). The drape body 12 may have any appropriate dimensions to lie on the body of a patient and support instruments thereon. It is also considered to mold a mesh (e.g., nylon mesh) into or on the drape body 12 to alter its structural integrity, or to provide tear-resistance to the drape body 12. However, the drape body 12 may be without such a nylon mesh.

When laid on the body of a patient, the drape body 12 conforms to the shape of the surface upon which it rests because of the flexible nature of its material. The drape body 12 is placed such that the undersurface 16 lies against the surface, whereas the top surface 14 is oriented upwardly.

Still referring to FIGS. 1 and 2, magnet units 20 are raised from a panel portion of the drape body 12 and therefore define the top surface 14 of the drape body 12, and are aligned in rows and columns. In another embodiment, the magnet units 20 are fully encapsulated in the material of the drape body 12, whereby the top surface of the magnetic mat 10 is flat. The magnetic units 20 typically comprise a permanent magnet or permanent magnets that may be encapsulated, sandwiched or embedded in the material of the drape body 12, and include a supporting shielding cup. The magnet units 20 are illustrated as being circular in FIGS. 1 and 2, but may have any other appropriate shape, such as a rectangle, a strip or a bar as shown hereinafter. Moreover, the arrangement of components of the magnet units 20 is described in further details hereinafter.

Accordingly, the presence of the permanent magnet units 20 in accordance with the embodiment of FIGS. 1 and 2 will allow ferromagnetic instruments to be retained on the magnetic drape 10 when placed thereon by medical personnel or any technician. The magnetic forces of the magnet units 20 will pull the instruments to the magnetic drape 10. The magnets of the magnet units 20 may for instance be ferrite ceramic magnets (e.g., anisotropic), among numerous possibilities, and may adopt any appropriate shape (e.g., circular, rectangular).

Referring to FIG. 2, there is illustrated the magnetic drape 10 of FIG. 1. It is observed that the thickness of the drape body 12, namely between the top surface 14 and the undersurface 16, is nonnegligible. It is known that the flux density of a magnetic field reduces in value as a function of a distance from the magnets. There is provided in FIG. 18 a graph illustrating a general trend of the magnetic flux density of the magnetic field as a function of a distance to a surface. Accordingly, by having the drape body 12 provided with a selected thickness, it is possible to have a minimal magnetic flux density under the undersurface 16.

Figure 3:
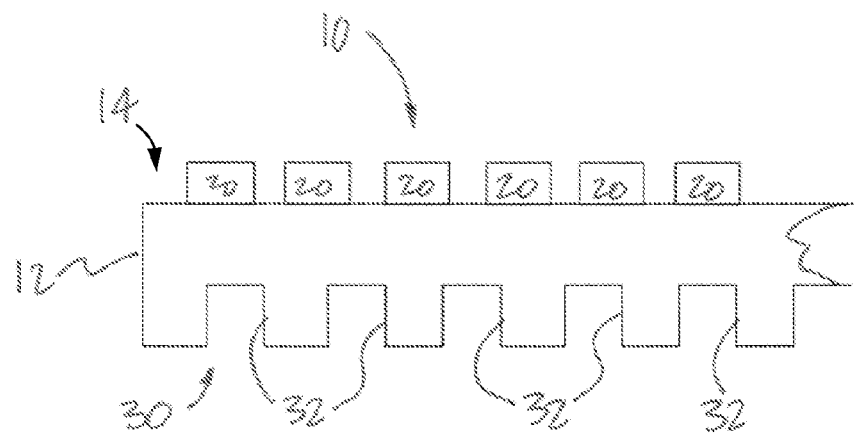
FIG. 3 is a schematic side view of a magnetic drape in accordance with another embodiment of the present disclosure, with longitudinal channels in an undersurface thereof.

Referring to FIG. 3, there is illustrated the drape body 12 with undersurface 30. The undersurface 30 has a plurality of longitudinal channels 32. The longitudinal channels 32 are provided so as to increase the distance between the top surface 14 and the undersurface 30 of the drape body 12, in view of having a minimal magnetic flux density at the undersurface 30, while increasing the flexibility of the mat 10. As there is less material above the longitudinal channels 32, the drape body 12 is more flexible. Alternative shapes are considered as well, such as posts, ribs or the like.

Figure 4:
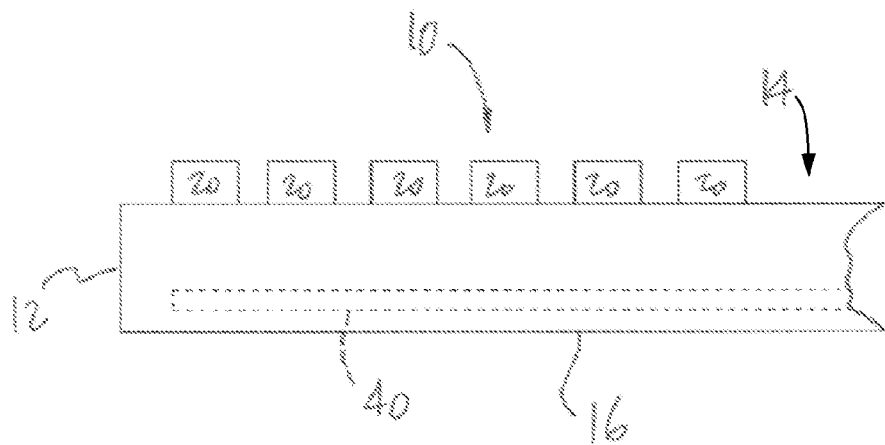
FIG. 4 is a schematic side elevation view of a magnetic drape with a shielding sheet or mesh sheet in accordance with another embodiment of the present disclosure.

Referring to FIG. 4, there is illustrated another embodiment of the magnetic drape 10, in which a shielding sheet 40 is provided in the drape body 12. The shielding sheet 40 may be laminated to the undersurface 16, or may simply be molded into the drape body 12. Although the shielding sheet 40 is illustrated as being closer to the undersurface 16 than the top surface 14, the shielding sheet 40 may be at any suitable location in the drape body 12. In such a case, the drape body 12 may consist of different layers bonded to one another, for instance to encapsulate shielding material therebetween. Alternatively, multiple layers of shielding sheets may also be used and as an example, one layer can be laminated closer to the undersurface while another can be closer to the top surface. Examples of materials used for the shielding sheet 40 include sheets of ferromagnetic material or of foil. It is for instance considered to use metal, numetal, powders, nano-materials, nano-metallurgical materials, such as nano-crystalline ferromagnetic cladding, among other possibilities. For instance, some embodiments of the Nanovate™ platforms by Integran may be used. Also, a mesh of shielding material (e.g., Nanovate™) may also be used.

It is considered to apply a phosphorescent or fluorescent coating to the magnetic mat 10, or to add a phosphorescent or fluorescent coating to the material of the drape body 12. Considering that some types of surgery are performed in minimal lighting, a magnetic mat 10 being phosphorescent or fluorescent will be visible to the medical personnel, showing an outline of the instruments.

Now that various arrangements of the magnetic drape 10 have been described, the configuration of the magnet units 20 are set forth. The magnet units 20 are constituted of one or more magnets supported on a shielding material which can be made of many materials such metal, numetal, powders, nano-materials, nano-metallurgical materials, such as nano-crystalline ferromagnetic cladding, among other possibilities. The various configurations are devised in order to produce a magnetic flux density of less than 10 Gauss at a given distance below the undersurface 16 of the magnetic drape 10. According to an embodiment, the magnetic flux density is less than 10 Gauss at a distance of ⅛ in from a bottom surface of the magnet units 20.

The various configurations comprise magnets made of any appropriate material. For instance, ceramic 8 or polymeric-based materials are well suited as a material for magnets for the magnet unit 20, in view of the required flux density of the magnetic field under the magnetic drape 10.

Figure 5A:
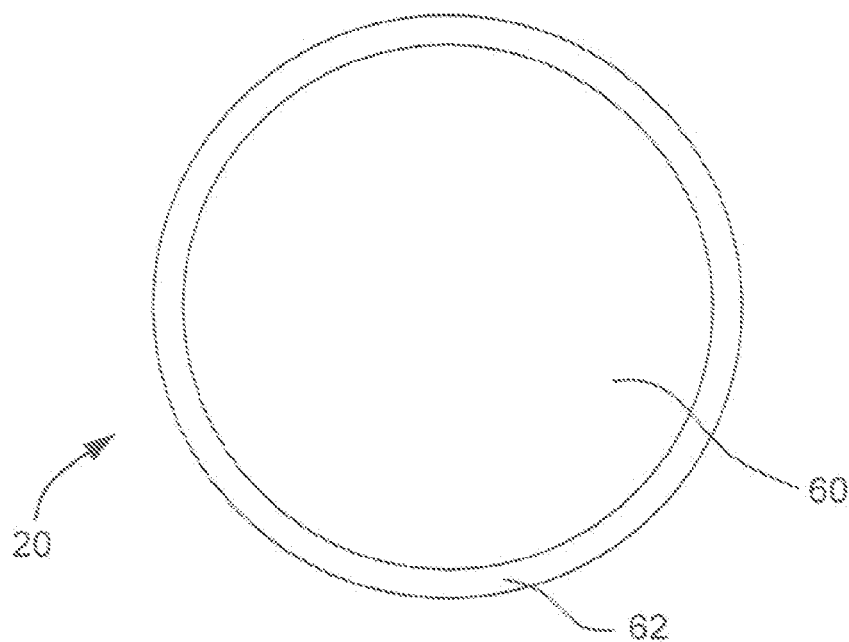
FIGS. 5A and 5B are respectively a schematic top view and side view of a magnet unit in accordance with an embodiment of the present disclosure, the magnet unit having a circular single permanent magnet suitably oriented and encapsulated in a metallic cup.
Figure 5B:
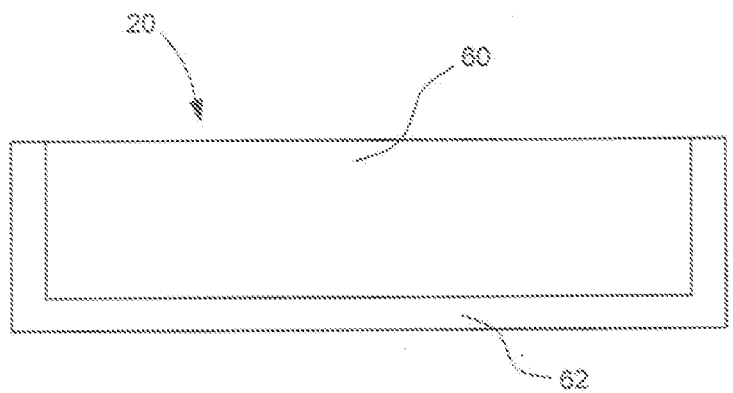

Referring to FIGS. 5A and 5B, a general arrangement of the magnet unit 20 is shown. The magnet unit 20 of FIG. 5A and 5B may be used in the magnetic drape 10 of FIGS. 1 to 4. The magnet unit 20 has at least one permanent magnet 60 encapsulated partially in a cup 62. The magnet 60 has at least a portion of its lateral surface and its bottom face within the cup 62, while the upper face is exposed. The cup 62 is made from a shielding material, such as mild steel (e.g., 1010 steel, 1018 steel), or any other appropriate material, whereby the magnetic flux density of the magnetic field is reduced away from the bottom face of the magnet 60. When the magnet unit 20 is positioned in the magnetic drape 10, the bottom face of the magnet 60 (hidden in the cup 62) is oriented toward the undersurface 16 (FIG. 1) of the magnetic drape 10.

By way of example, the cup 62 has a wall thickness ranging between 0.02-0.06 in (although other thicknesses are possible), with an outer diameter of 0.86 in, although other outer diameters are possible. Depending on the thickness of the wall of the cup 62, the magnet 60 has a diameter ranging between 0.74-0.82 in, with the magnet 60 being snugly or force-fittingly received in the cup 62. A suitable height for the combination of the magnet 60 and cup 62 is 0.16 in, with the magnet 60 and cup 62 concurrently defining a top planar surface of the magnet unit 20.

Figure 6A:
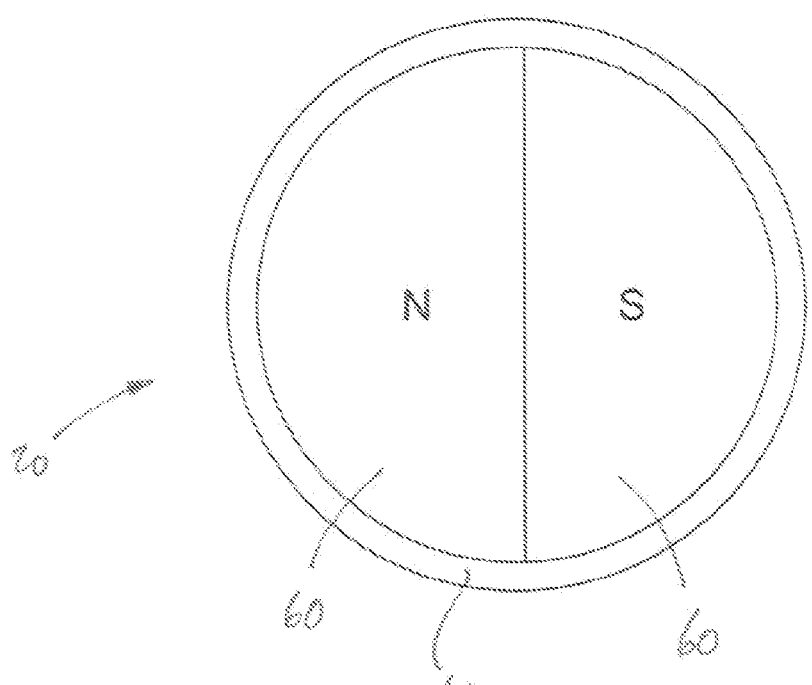
FIGS. 6A and 6B are schematic top and side views of the magnet unit of FIGS. 5A and 5B, featuring hemi-spherical sections exposing opposed poles at the top of a cup.
Figure 6B:
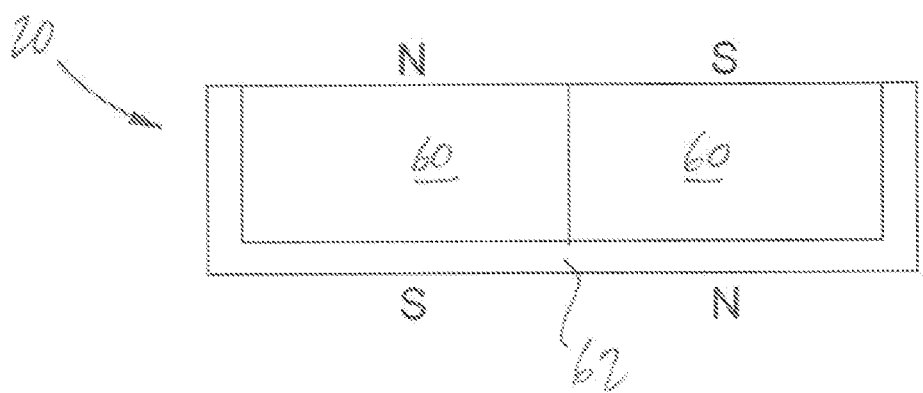

Referring to FIGS. 6A and 6B, a configuration of the magnet unit 20 is shown, using the specifications (e.g., dimensions and materials) set forth with the general arrangement of FIGS. 5A and 5B. In the configuration of FIGS. 6A and 6B, the cup 62 supports a bi-polar vertically magnetized magnet 60, with the magnet 60 exposing opposite poles on the top surface of the magnet unit 20, as illustrated by N and S. As observed in FIG. 6B, the magnet 60 has two sections, with each section arranged to have a first pole oriented toward the top surface of the magnet unit 20, and an opposite pole oriented toward the bottom surface of the magnet unit 20.

It is pointed out that the vertical direction is between the top surface 14 and the undersurface 16, but it not necessarily representative of the orientation in which the drape 10 will be used. The drape 10 may indeed be inclined, or even have a portion that is hanging vertically.

Further examples are provided, but in the various embodiments, the magnet 60 must have at least two sections of opposite poles exposed at the top surface of the magnet 60, which poles are produced by way of a magnetization process. Alternatively, the sections may be physically independent magnets in a same cup 62, with the independent magnets reproducing any one of the pole arrangements described herein. For simplicity purposes, both embodiments of a single magnet with multiple sections, or multiple independent magnets in a same cup 62 will be referred to as sections of magnets, with the sections having a specific polarity arrangement to produce a magnetic flux density in accordance with the present invention.

Figure 7:
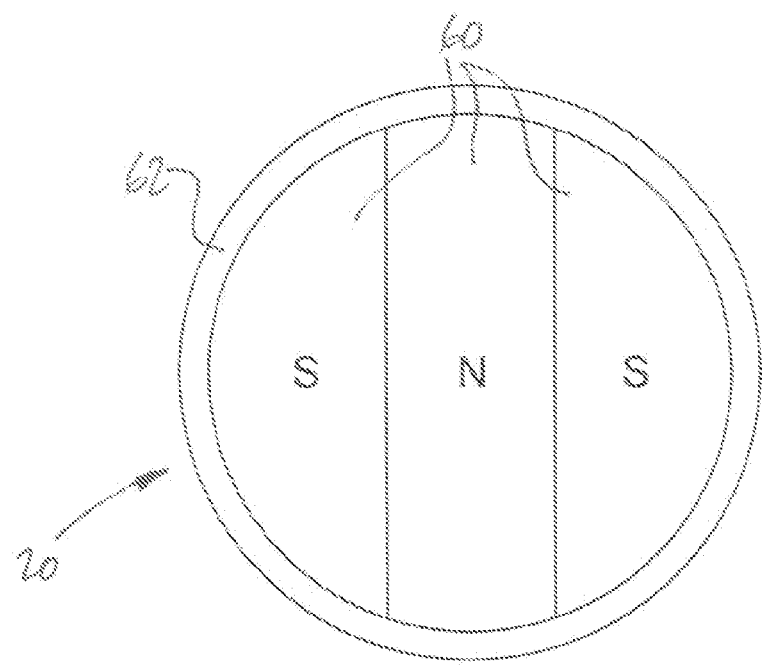
FIG. 7 is a schematic top view of the magnet unit of FIG. 5A, featuring elongated sections exposing opposed poles at the top of the cup.

Referring to FIG. 7, another configuration of the magnet unit 20 is shown. In the configuration of FIG. 7, the cup 62 supports the magnet 60, with the magnet 60 having three vertically magnetized sections of alternating opposite poles on the top surface (N-S-N) of the magnet unit 20, as illustrated by N and S. In similar fashion to the magnet unit 20 observed in FIG. 6B, each of the sections of the magnet 60 is arranged to have a first pole oriented toward the top surface of the magnet unit 20, and an opposite pole oriented toward the bottom surface of the magnet unit 20.

Figure 8:
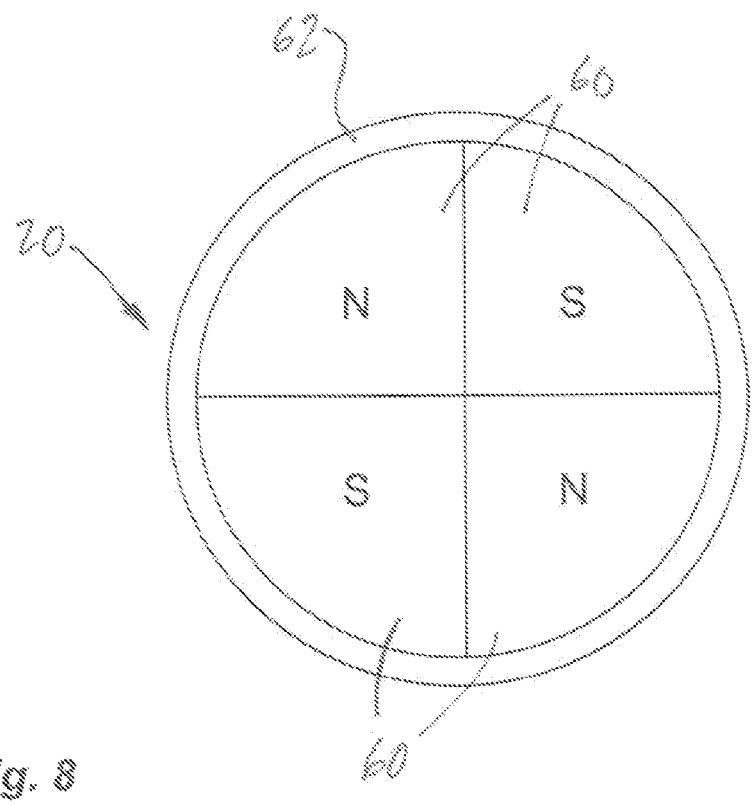
FIG. 8 is a schematic top view of the magnet unit of FIG. 5A, featuring quarter-shaped sections exposing opposed poles at the top of the cup.

Referring to FIG. 8, another configuration of the magnet unit 20 is shown. In the configuration of FIG. 8, the cup 62 supports the magnet 60 having four quarter-shaped vertically magnetized sections exposing a sequence of alternating opposite poles (N-S-N-S) on the top surface of the magnet unit 20, as illustrated by N and S. In similar fashion to the magnet unit 20 observed in FIG. 6B, each of the sections of the magnets 60 is arranged to have a first pole oriented toward the top surface of the magnet unit 20, and an opposite pole oriented toward the bottom surface of the magnet unit 20.

Figure 9:
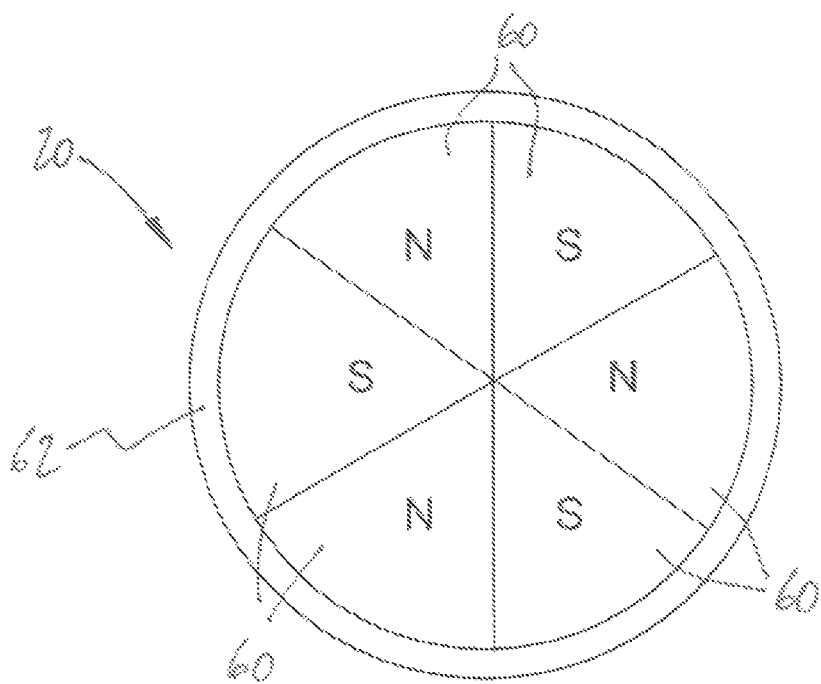
FIG. 9 is a schematic top view of the magnet unit of FIG. 5A, featuring sixth-shaped sections exposing opposed poles at the top of the cup.

Referring to FIG. 9, another configuration of the magnet unit 20 is shown. In the configuration of FIG. 9, the cup 62 supports the magnet 60 with sixth-shaped vertically magnetized sections, with the sixth-shaped sections of the magnets 60 exposing a sequence of alternating opposite poles (N-S-N-S-N-S) on the top surface of the magnet unit 20, as illustrated by N and S. In similar fashion to the magnet unit 20 observed in FIG. 6B, each of the sections of the magnet 60 is arranged to have a first pole oriented toward the top surface of the magnet unit 20, and an opposite pole oriented toward the bottom surface of the magnet unit 20.

Figure 10:
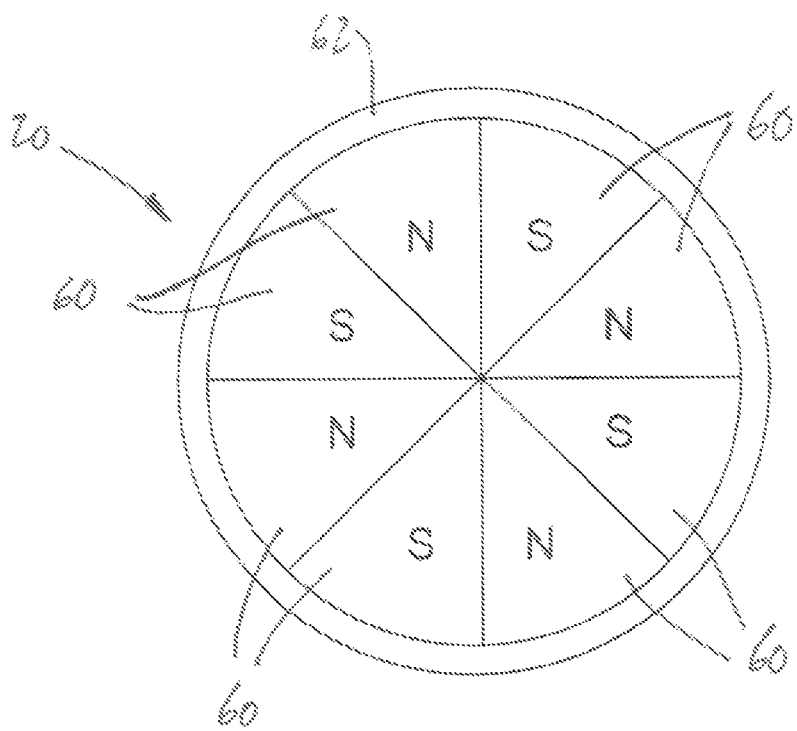
FIG. 10 is a schematic top view of the magnet unit of FIG. 5A, featuring eighth-shaped sections exposing opposed poles at the top of the cup.

Referring to FIG. 10, another configuration of the magnet unit 20 is shown. In the configuration of FIG. 10, the cup 62 supports the magnet 60 with eighth-shaped vertically magnetized sections, with the eighth-shaped segments exposing a sequence of alternating opposite poles (N-S-N-S-N-S-N-S) on the top surface of the magnet unit 20, as illustrated by N and S. In similar fashion to the magnet unit 20 observed in FIG. 6B, each of the segments 60 is arranged to have a first pole oriented toward the top surface of the magnet unit 20, and an opposite pole oriented toward the bottom surface of the magnet unit 20.

Figure 11A:
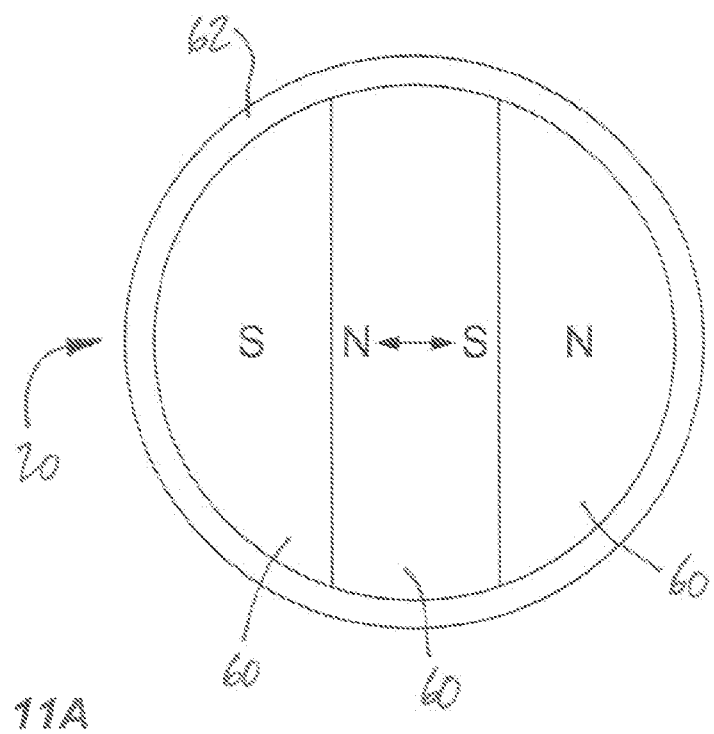
FIGS. 11A and 11B are schematic top and side views of the magnet unit of FIG. 5A, featuring elongated lateral sections exposing opposed poles at the top of the cup, with a central section creating a Halbach effect.
Figure 11B:
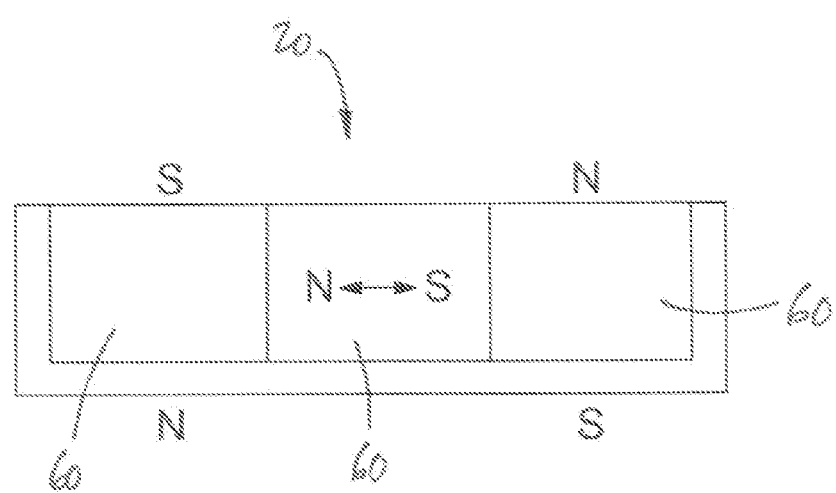

Referring to FIGS. 11A and 11B, another configuration of the magnet unit 20 is shown. In the configuration of FIGS. 11A and 11B, the cup 62 supports the magnet 60 having three magnetized segments in similar fashion to FIG. 7. However, the configuration of FIGS. 11A and 11B differs from the configuration of FIG. 7, in that the magnets 60 are in a striped Halbach pattern. In the Halbach pattern, the central section of the magnets 60 is oriented sideways to have both north and south poles exposed from the top surface of the magnet unit 20. The north pole of the central section of the magnet 60 is adjacent to an exposed south pole of a lateral section of the magnets 60, whereas the south pole of the central section of magnet 60 is adjacent to an exposed north pole of the other lateral section of the magnet 60, as illustrated by N and S. As shown in FIG. 11B, the lateral sections of magnets 60 are arranged to have a first pole oriented toward the top surface of the magnet unit 20, and an opposite pole oriented toward the bottom surface of the magnet unit 20.

Other configurations are possible for the magnet unit 20 with a circular shape. For instance, the magnets 60 may be in a tenth-shaped sections configuration, or may even feature more magnet sections.

Figure 12A:
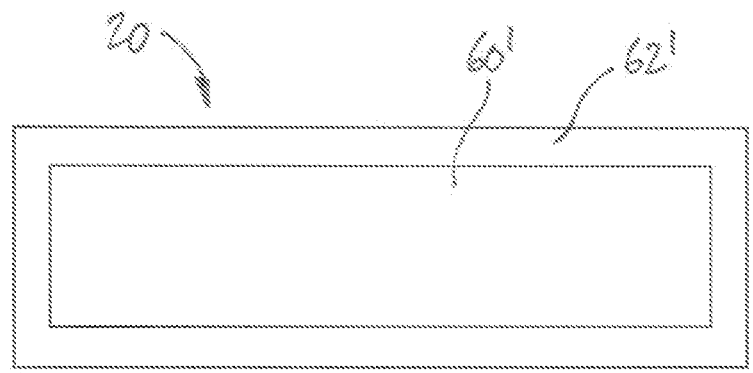
FIGS. 12A and 12B are respectively a schematic top view and side view of a magnet unit used in accordance with an embodiment of the present disclosure, the magnet unit having a rectangular single permanent magnet suitably oriented and encapsulated in a metallic cup.
Figure 12B:
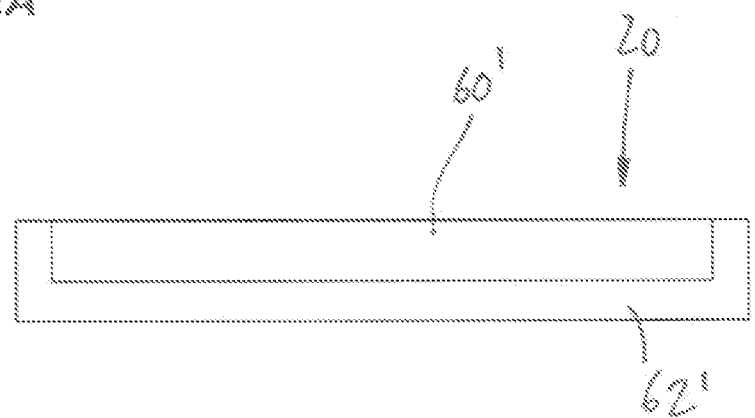

Referring to FIGS. 12A and 12B, the magnet unit 20 has a rectangular, strip or bar shape as opposed to a circular one. A general arrangement of the rectangular magnet unit 20 is shown in FIGS. 12A and 12B. The magnet unit 20 of FIG. 12A and 12B may be used in the magnetic drape 10 of FIGS. 1 to 4. The magnet unit 20 has at least one permanent magnet 60' encapsulated partially in a cup 62'. The single magnet 60' must be magnetized so as to have at least two opposite poles in the top surface of the magnet 60'.

The magnet 60' has at least a portion of its side surfaces and its bottom face within the cup 62', while the upper face is exposed. The cup 62' is made from a shielding material, such as mild steel (e.g., 1010 steel, 1018 steel), or any other appropriate shielding material, whereby the magnetic flux density of the magnetic field is reduced away from the bottom face of the magnet 60'. When the magnet unit 20 of FIGS. 12A and 12B is positioned in the magnetic drape 10, the bottom face of the magnet 60' (hidden in the cup 62') is oriented toward the undersurface 16 (FIG. 1) of the magnetic mat 10.

By way of example, the cup 62' has a wall thickness ranging between 0.02-0.06 in, with a length of 1.62 in and a width of 0.5 in, although other dimensions are possible. A suitable height for the combination of the magnet 60' and cup 62' is 0.1 in, although other dimensions are possible, with the magnet 60' and cup 62' concurrently defining a top planar surface of the magnet unit 20.

Figure 13:
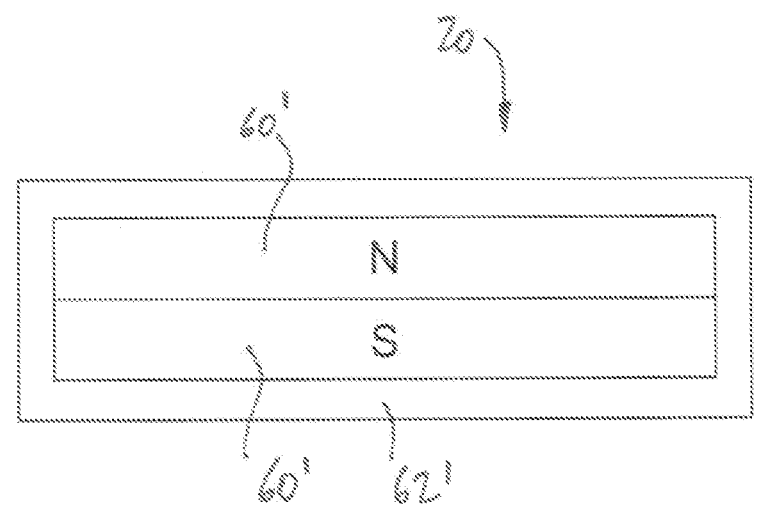
FIG. 13 is a schematic top view of the magnet unit of FIGS. 12A and 12B, featuring elongated sections exposing opposed poles at the top of the cup.

Referring to FIG. 13, a rectangular configuration of the magnet unit 20 is shown. In the configuration of FIG. 13, the cup 62' supports a pair of elongated sections of the magnet 60', with the elongated sections of the magnet 60' exposing opposite poles on the top surface of the magnet unit 20, as illustrated by N and S. Each of the sections of the magnet 60' is arranged to have a first pole oriented toward the top surface of the magnet unit 20, and an opposite pole oriented toward the bottom surface of the magnet unit 20.

Figure 14A:
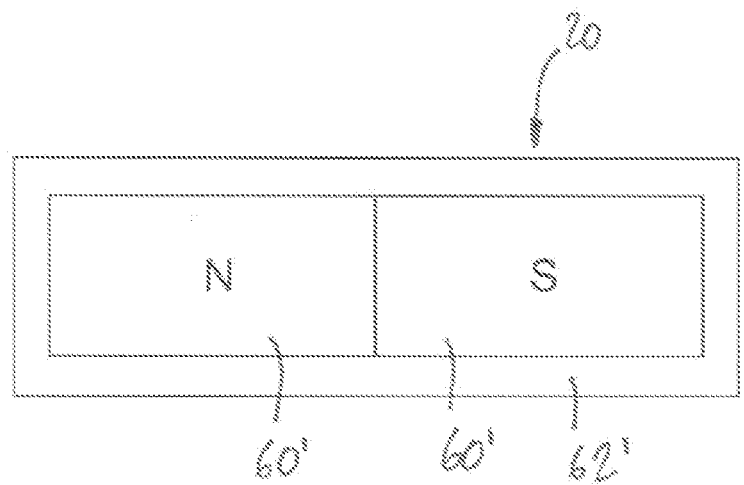
FIGS. 14A and 14B are schematic top and side view of the magnet unit of FIGS. 12A and 12B, featuring rectangular sections exposing opposed poles at the top of the cup.
Figure 14B:
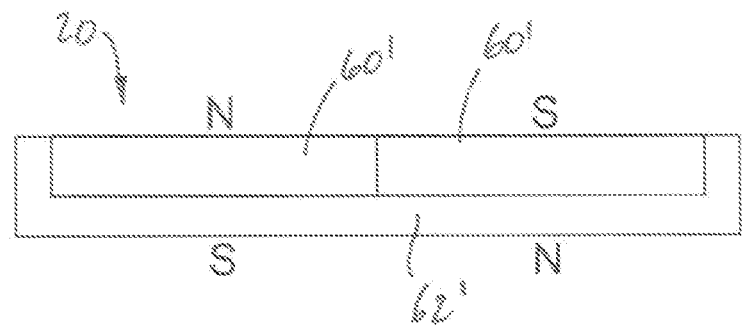

Referring to FIGS. 14A and 14B, another configuration of the magnet unit 20 is shown. In the configuration of FIG. 14A and 14B, the cup 62' supports a pair of rectangular sections of the magnet 60', with the rectangular sections of the magnet 60' exposing opposite poles on the top surface of the magnet unit 20, as illustrated by N and S. As shown in FIG. 14B, each of the sections of the magnet 60' is arranged to have a first pole oriented toward the top surface of the magnet unit 20, and an opposite pole oriented toward the bottom surface of the magnet unit 20.

Figure 15:
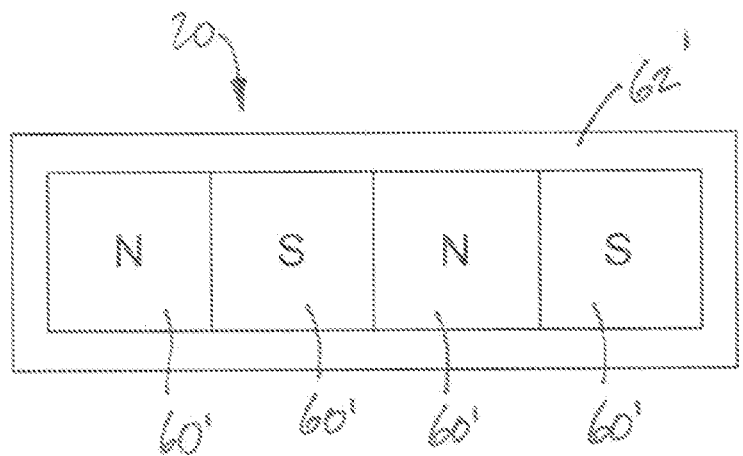
FIG. 15 is a schematic top view of the magnet unit of FIGS. 12A and 12B, featuring four rectangular sections exposing opposed poles at the top of the cup.

Referring to FIG. 15, another configuration of the magnet unit 20 is shown. In the configuration of FIG. 14A and 14B, the cup 62' supports four square sections of the magnet 60', with the square sections of the magnet 60' exposing alternating opposite poles (N-S-N-S) on the top surface of the magnet unit 20, as illustrated by N and S. Each of the sections of the magnet 60' is arranged to have a first pole oriented toward the top surface of the magnet unit 20, and an opposite pole oriented toward the bottom surface of the magnet unit 20.

Figure 16:
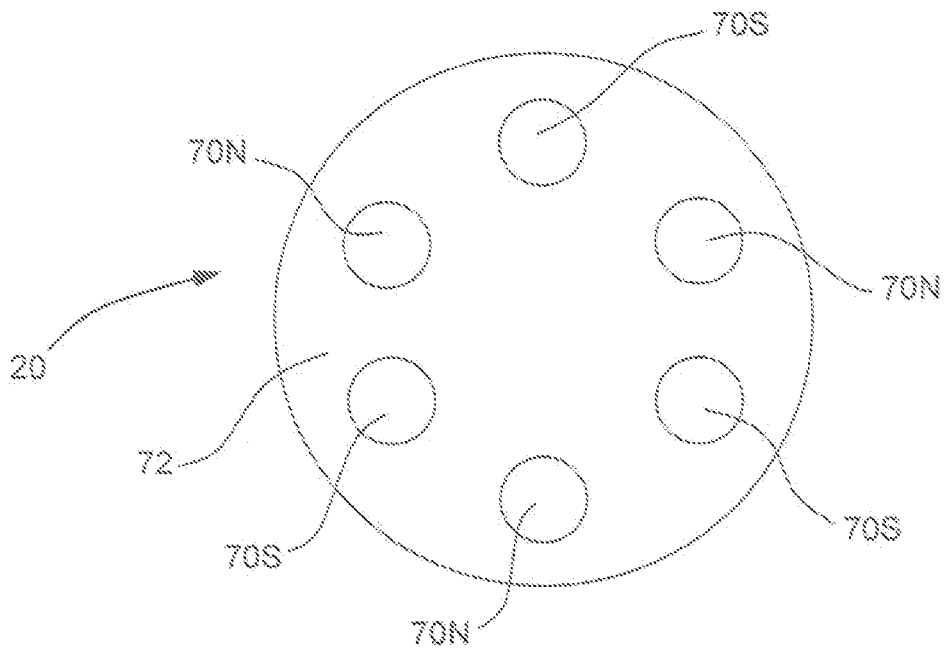
FIG. 16 is a schematic top view of a magnet unit having cavities with circular magnet sections exposing opposed poles at the top of the cup.
Figure 17:
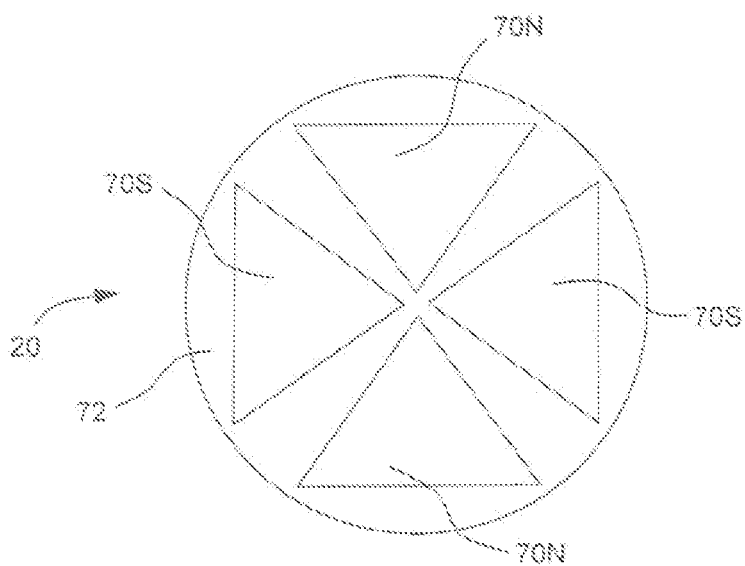
FIG. 17 is a schematic top view of a magnet unit having cavities with triangular magnet sections exposing opposed poles at the top of the cup.

Referring to FIGS. 16 and 17, yet another embodiment of the magnet unit 20 is shown. The magnet unit 20 of FIGS. 16 and 17 may be used in the magnetic mat 10 of FIGS. 1 to 4. The magnet unit 20 comprises a plurality of smaller permanents magnets 70N and 70S, with the affixed N indicating a North polarity while the affixed S indicates a South polarity. The magnets 70 are each received in a respective cavity in a metallic cup 72. The magnets 70 each have their lateral portion and their bottom face within a respective cavity of the cup 72, while the upper face is exposed. The metallic cup 72 is made from a shielding material, such as 1018 steel, or any other appropriate material, whereby the magnitude of the magnetic field is reduced away from the bottom face of the magnets 70. When the magnet unit 20 of FIGS. 7A and 7B is positioned in the magnetic mat 10, the bottom faces of the magnets 70 (hidden in the cup 72) are oriented toward the undersurface 16 (FIG. 1) of the magnetic mat 10.

In FIG. 16, the magnet unit 20 comprises six magnets 70, although a magnet unit 20 may comprise more or less permanent magnets. Moreover, the magnets 70 are shown in an alternating polarity about the magnet unit 20. The magnets 70 are also arranged with diametrically opposed polarities, although other arrangements may also be suitable.

Also, the magnets 70 are illustrated as being circular, but may have other geometries. For instance, a plurality of pie-shaped magnets 70 may share one common circular cavity in the cup 72, as illustrated in FIG. 17.

The permanent magnets 20, 60 and 70 are made of any suitable magnetic material. One type of permanent magnet that may be used in the magnetic drape 10 is a standard or commercial ferrite magnets, although samarium-cobalt magnets (model 26002, Grade 24, with 2% samarium and 17% cobalt from Armstrong Magnetics Inc.) may also be used. As for the cups 60 and 70, they may be machined, cast, molded, etc.

In any of the embodiments of FIGS. 1 to 17, there may be provided on the undersurface 16 of the magnetic drape 10 a logo, an icon, instructions or the like, to indicate that the mat 10 is upside down. The mat 10 should be used with the magnets 20 facing upwardly. These instructions may also be on the top surface 14 to indicate that the mat 10 is correctly installed. In an embodiment, these instructions are printed directly on the surfaces of the magnetic drape 10.

Figure 18:
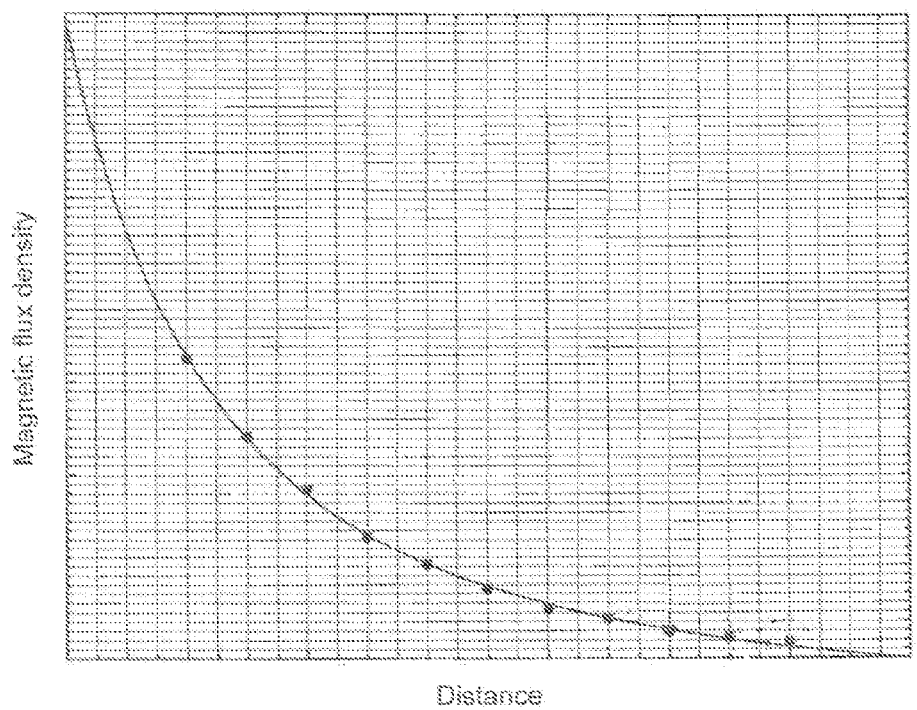
FIG. 18 is a graph illustrating a general trend of magnetic flux density as a function of a distance from a magnet.

Referring to FIG. 18, a graph illustrates a relation between a distance and a magnetic flux density. According to the graph, an increase in distance from the magnet units 20 (e.g., below the undersurface 16 of the drape 10) results in a decrease in the magnetic flux density. Accordingly, the drape 10 may have an increased thickness under the magnet units 20 so as to ensure that the magnetic flux density is below a predetermined value. The afore-described embodiments allow the magnetic drape 10 to maintain a magnetic flux density of less than 10 Gauss at a distance of ⅛ in below the bottom surface of the magnet units 20. If a lower magnetic flux density is required, the thickness of the panel of the drape body 12 may be increased.

The above-described embodiments may be for single-use magnetic drapes or for sterilizable magnetic drapes that will be reused. The embodiments described above may be used individually, or in combination where applicable.

The invention claimed is:

1. magnetic drape comprising:
    a drape body made of a flexible material, the drape body having a panel portion having an undersurface adapted to be laid on an uneven body and a top surface, and a given thickness between the undersurface and the top surface; and
    a plurality of magnet units within the flexible material of the drape body, with each said magnet unit comprising a shielding material in the shape of a cup oriented to have a bottom wall facing toward the undersurface of the drape body, and at least one magnet received at least partially in the cup, the at least one magnet comprising at least two sections arranged to expose opposite polarity on a top surface of the magnetic drape, with each said section having opposite polarities oriented vertically.

2. The magnetic drape according to claim 1, wherein the magnet units each have any one of a circular shape and a rectangular shape.

3. The magnetic drape according to claim 2, wherein the cups each have a circular shape, and further comprising two sections of magnets in each said cup, each said section having a semi-circular shape.

4. The magnetic drape according to claim 2, wherein the cups each have a circular shape, and further comprising four sections of magnets in each said cup, each said section having a quarter shape, with the sections exposing a N-S-N-S sequence of opposite poles in the top surface of the magnet unit.

5. The magnetic drape according to claim 2, wherein the cups each have a circular shape, and further comprising six sections of magnets in each said cup, each said section having a sixth shape, with the sections exposing a N-S-N-S-N-S sequence of opposite poles in the top surface of the magnet unit.

6. The magnetic drape according to claim 2, wherein the cups each have a circular shape, and further comprising eight said sections in each said cup, with the sections exposing a N-S-N-S-N-S-N-S sequence of opposite poles in the top surface of the magnet unit.

7. The magnetic drape according to claim 2, wherein the cups each have a circular shape, and further wherein the at least one magnet comprises three sections in each said cup, each said section having an elongated shape with the sections arranged side by side to define a circular shape, with the magnets exposing a sequence of opposite poles in the top surface of the magnet unit.

8. The magnetic drape according to claim 2, wherein the cups each have a circular shape, and further wherein the at least one magnet comprises three sections in each said cup, each said section having an elongated shape with the sections arranged side by side to define a circular shape, with lateral sections exposing opposite poles in the top surface of the magnet unit, and a central section being oriented relative to the lateral sections to create a Halbach effect.

9. The magnetic drape according to claim 2, wherein the cups each have a rectangular shape, and wherein the at least one magnet comprises two sections in each said cup, each said section having an elongated shape with the sections arranged side by side to define a rectangular shape.

10. The magnetic drape according to claim 2, wherein the cups each have a rectangular shape, and wherein the at least one magnet comprises two sections in each said cup, each said section having a square shape with the sections arranged side by side to define a rectangular shape.

11. The magnetic drape according to claim 2, wherein the cups each have a rectangular shape, and wherein the at least one magnet comprises four sections in each said cup, each said section having a square or rectangular shape with the sections arranged side by side to define a rectangular shape.

12. The magnetic drape according to claim 2, wherein the cups each have a circular shape with at least two cavities, and further comprising one of said sections of magnet in each said cavity of the cups.

13. The magnetic drape according to claim 12, wherein the cavities have one of a circular shape and a triangular shape.

14. The magnetic drape according to claim 1, wherein the magnet units project upwardly from the top surface of the panel portion of the drape body.

15. The magnetic drape according to claim 14, wherein the given thickness of the panel portion is at least ⅛ in such that a magnetic flux density at the undersurface of the drape body is less than 10 Gauss.

16. The magnetic drape according to claim 14, wherein the given thickness of the panel portion is sized to keep the magnet units at a distance of at least ⅛ in from an electronic device in a patient when the magnetic drape is laid on the patient, such that a magnetic flux density is less than 10 Gauss at the electronic device.

17. The magnetic drape according to claim 1, further comprising shielding means connected to or incorporated in the drape body below the plurality of magnet units.

18. The magnetic drape according to claim 17, wherein the shielding means is at least one of a shielding sheet, a shielding mesh, a shielding material, and shielding particles.

19. The magnetic drape according to claim 1, further comprising at least one of a fluorescent and phosphorescent coating or additive on the top surface of the drape body.

* * * * *